(12) United States Patent
Lawrence et al.

(10) Patent No.: US 7,637,901 B2
(45) Date of Patent: Dec. 29, 2009

(54) MALLEABLE CANNULA

(75) Inventors: Robert J. Lawrence, Grand Rapids, MI (US); Frederick A. Shorey, East Grand Rapids, MI (US); Donald R. Sandmore, Newaygo, MI (US)

(73) Assignee: Medtronic, Inc., Minneapolis, MN (US)

( * ) Notice: Subject to any disclaimer, the term of this patent is extended or adjusted under 35 U.S.C. 154(b) by 250 days.

(21) Appl. No.: 11/284,576

(22) Filed: Nov. 22, 2005

(65) Prior Publication Data

US 2006/0074402 A1 Apr. 6, 2006

Related U.S. Application Data

(62) Division of application No. 10/285,314, filed on Oct. 31, 2002, now Pat. No. 6,976,979.

(51) Int. Cl.
*A61M 25/00* (2006.01)
(52) U.S. Cl. ...................................................... 604/524
(58) Field of Classification Search ............. 604/93.01, 604/264, 523–529, 533; 600/139, 407; 138/118
See application file for complete search history.

(56) References Cited

U.S. PATENT DOCUMENTS

| | | | |
|---|---|---|---|
| 4,129,129 A | 12/1978 | Amrine | |
| 4,639,252 A | 1/1987 | Kelly et al. | |
| 4,863,441 A | 9/1989 | Lindsay et al. | |
| 4,976,688 A | 12/1990 | Rosenblum | |
| 5,222,949 A | 6/1993 | Kaldany | |
| 5,269,752 A | 12/1993 | Bennett | |
| 5,360,406 A | 11/1994 | Boykin et al. | |
| 5,405,338 A | 4/1995 | Kranys | |
| 5,423,745 A | 6/1995 | Todd et al. | |
| 5,454,787 A * | 10/1995 | Lundquist | 604/95.01 |
| 5,704,926 A | 1/1998 | Sutton | |
| 5,765,568 A | 6/1998 | Sweezer, Jr. et al. | |
| 5,769,828 A | 6/1998 | Jonkman | |
| 5,807,326 A | 9/1998 | O'Neill et al. | |
| 5,984,908 A | 11/1999 | Davis et al. | |
| 6,016,848 A * | 1/2000 | Egres, Jr. | 138/137 |
| 6,030,356 A | 2/2000 | Carlson et al. | |
| 6,042,576 A | 3/2000 | DeVries | |
| 6,066,125 A * | 5/2000 | Webster, Jr. | 604/528 |
| 6,146,371 A | 11/2000 | DeWindt et al. | |
| 6,152,911 A * | 11/2000 | Giannoble | 604/524 |
| 6,197,014 B1 | 3/2001 | Samson et al. | |
| 6,319,244 B2 | 11/2001 | Suresh et al. | |
| 6,440,120 B1 | 8/2002 | Maahs | |
| 6,447,484 B1 | 9/2002 | Briscoe et al. | |
| 6,544,215 B1 | 4/2003 | Bencini et al. | |
| 6,976,979 B2 | 12/2005 | Lawrence et al. | |

* cited by examiner

*Primary Examiner*—Nicholas D Lucchesi
*Assistant Examiner*—Christopher D Koharski
(74) *Attorney, Agent, or Firm*—Mike Jaro; Jeffrey J. Hohenshell

(57) ABSTRACT

A malleable cannula has a body with a proximal end and a distal end, the body having a wall defining a lumen extending from the proximal end to the distal end. A reinforcement member extends along the lumen, the reinforcement member having an interior side facing the lumen and an exterior side facing away from the lumen. A malleable member extends along a portion of the exterior side of the reinforcement member. The malleable member may be constructed of a tube with a wire slidably received within the tube and may include an anchor.

8 Claims, 4 Drawing Sheets

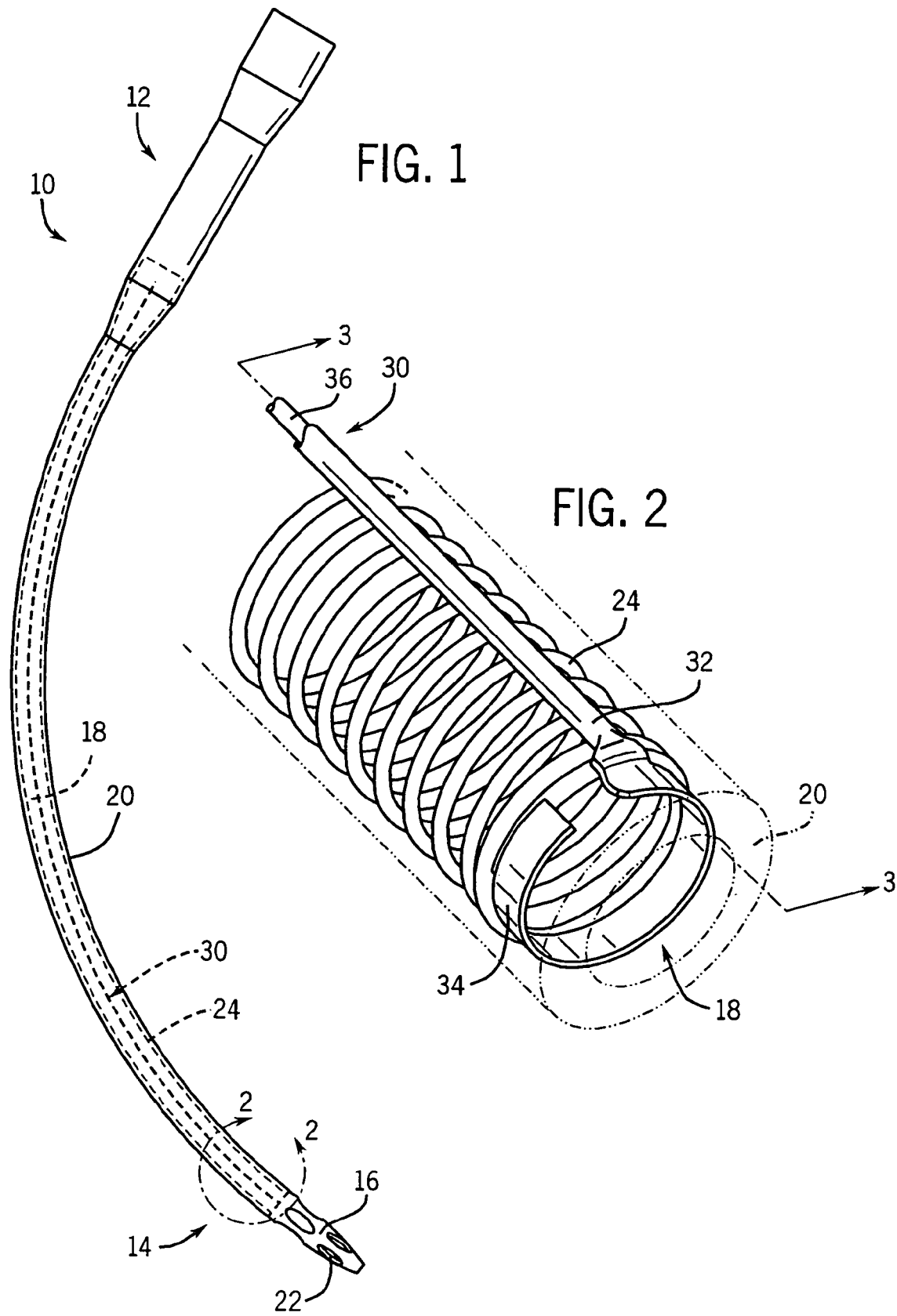

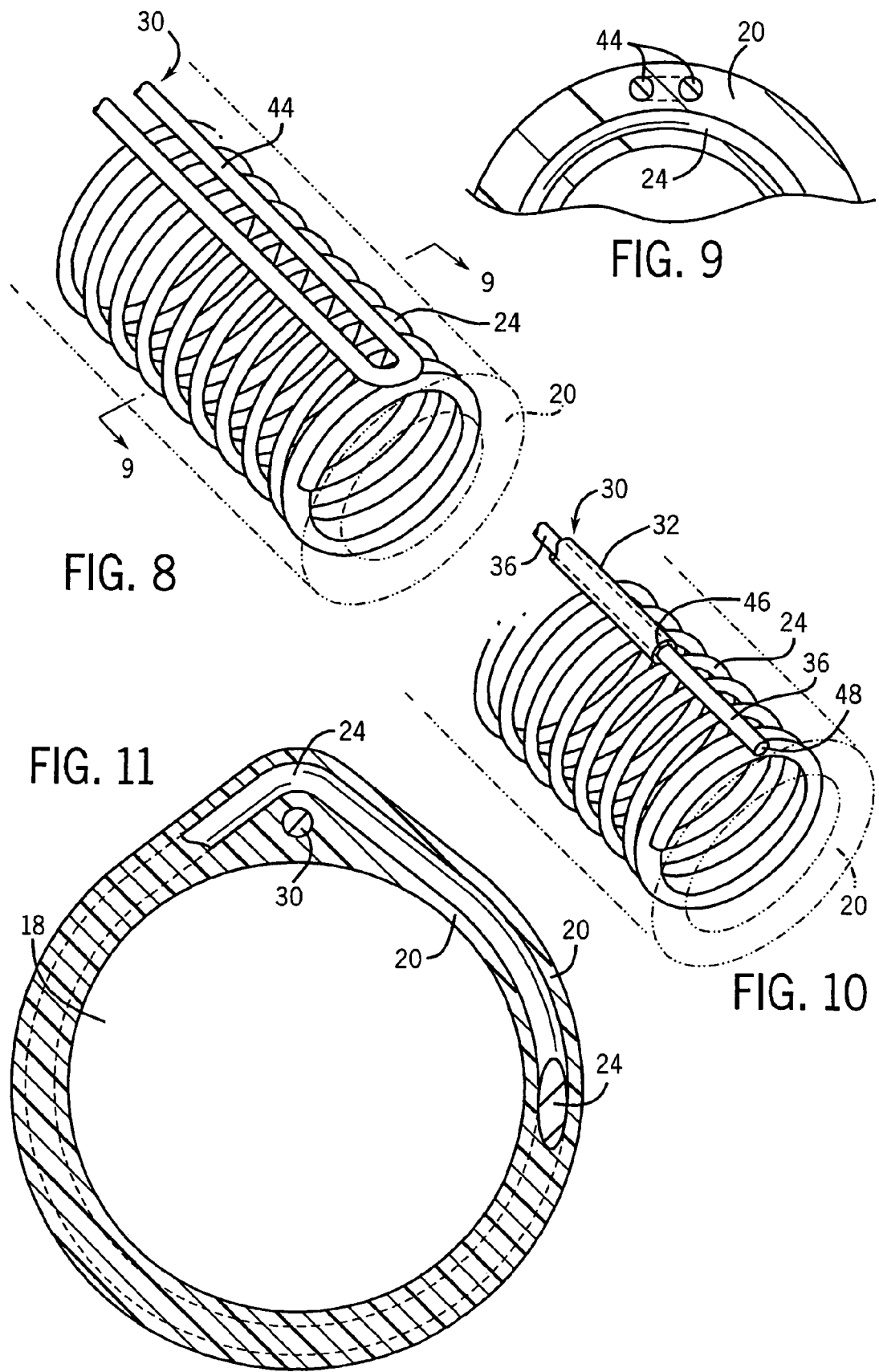

MALLEABLE CANNULA

This patent application is a divisional of U.S. patent application Ser. No. 10/285,314, filed Oct. 31, 2002, now U.S. Pat. No. 6,976,979 and entitled "Malleable Cannula."

FIELD OF THE INVENTION

Background of the Invention

During cardiac surgery, circulation of blood through a patient's body may be maintained by connecting the patient to an extracorporeal system, such as a heart-lung machine. The heart-lung machine adds oxygen to and removes carbon dioxide from the blood, heats or cools the blood, and provides impetus to the blood to cause the blood to circulate through the patient's vascular system.

Connecting a patient to a extracorporeal system is typically done by inserting a cannula into the patient's venous system near or in the heart to remove blood from the patient and direct it to the extracorporeal circuit. After the blood has passed through the extracorporeal circuit, the blood is infused into the patient's arterial system near the heart.

The venous cannula that is inserted into the heart to siphon blood away for entry into the heart-lung machine is typically inserted into the right atrium and/or vena cava. The venous cannula may be a single stage device having one set of input apertures or a two-stage device used to simultaneously drain the right atrium and superior vena cava through an atrial basket while the inferior vena cava is drained through another set of apertures at the distal tip of the cannula. Oxygenated blood is returned to the heart from the heart-lung machine using an arterial cannula to return blood to the aorta.

In order to maintain proper blood flow rate through a cannula, the cannula body typically has a wire support, such as a helical reinforcement spring to prevent kinking or other degradation of the lumen extending through the cannula body. Additionally, it is often desired to have a malleable cannula that may be bent into a particular configuration and that maintains the chosen configuration during use. Such malleability may be provided by the inclusion of a malleable member, such as a relatively stiff wire extending along the length of the cannula body, the malleable member maintaining the cannula in a particular shape chosen by the surgeon.

The construction of a suitable malleable cannula presents certain design challenges. The addition of a malleable member may compromise the cross-sectional area of the lumen, thus degrading the flow rate provided by a particular size cannula. For example, a cannula having a particular outside diameter may have a 25-35 percent reduction in flow through the lumen when a malleable member is added to the design. Accordingly, to achieve the same flow rate, a cannula having a larger outside diameter may need to be chosen, which may not be desirable given the larger aperture necessary for insertion of the larger cannula into a particular portion of the heart.

Another design issue that arises with respect to the addition of a malleable member to a cannula is the issue of how to anchor the malleable member within the cannula body. Although a cannula is typically molded of a plastic material that will help to keep a malleable wire in place, when the cannula body is bent and twisted in a variety of directions by the surgeon during use, the wire may shift in the cannula body due to the changing curvature of the outer wall of the cannula. Further, movement of the malleable wire with respect to the cannula wall may result in damage to the cannula wall by the wire and the possible puncture of the cannula wall by the wire under certain circumstances.

There is a need for a cannula that is malleable but does not have a reduction in the flow rate for a given size cannula. Further, there is a need for a method and apparatus for improved anchoring of a malleable member within a cannula body. Further, there is a need for malleable member that is configured to not permit damage to the cannula wall by movement of the malleable member when the cannula is shaped during use.

It would be desirable to provide a system and/or method that provides one or more of these or other advantageous features. Other features and advantages will be made apparent from the present specification. The teachings disclosed herein extend to those embodiments that fall within the scope of the appended claims, regardless of whether they accomplish one or more of the aforementioned needs.

SUMMARY OF THE INVENTION

The invention relates to a malleable cannula. The malleable cannula has a body with a proximal end and a distal end, the body having a wall defining a lumen extending from the proximal end to the distal end. A reinforcement member extends along the lumen, the reinforcement member having an interior side facing the lumen and an exterior side facing away from the lumen. A malleable member extends along a portion of the exterior side of the reinforcement member, the malleable member adapted to retain the body in a custom shape after the body is bent into the custom shape and includes a tube and a wire slidably received within the tube.

The invention further relates to a malleable cannula having a body with a proximal end and a distal end, the body having a wall defining a lumen extending from the proximal end to the distal end. A reinforcement spring extends along the lumen, the reinforcement spring having an interior side facing the lumen and an exterior side facing away from the lumen. A malleable member extends along at least a portion of the exterior side of the reinforcement spring, the malleable member adapted to retain the body in a custom shape after the body is bent into the custom shape. The malleable cannula further includes means for anchoring the malleable member within the wall, the means for anchoring limiting the travel of the malleable member with respect to the wall when the cannula is manipulated.

The invention further relates to a malleable cannula having a body with a wall with an annular cross-section defining a lumen extending from a proximal portion of the body to a distal portion of the body. A reinforcement spring extends along a portion of the lumen. A malleable member is incorporated into the wall, the malleable member having a first portion and an anchor attached to and extending from the first portion, the anchor adapted to substantially inhibit movement of the malleable member within the wall.

Further still, the invention relates to a method of making a malleable cannula. The method includes the steps of providing a mandrel and a quantity of molten plastic material, dipping the mandrel in the plastic material to coat the mandrel with a first layer of the plastic material, and curing the first layer. The method further includes the steps of sliding a reinforcement spring over the first layer, providing a malleable member having an anchor at a distal end thereof, coupling the malleable member to the exterior side of the reinforcement spring, and dipping the mandrel into the plastic material to coat the mandrel with a second layer of the plastic material.

The invention further relates to a malleable cannula having a body with a proximal end and a distal end, the body having a wall defining a lumen extending from the proximal end to the distal end. The cannula further includes a reinforcement spring extending along the lumen, the reinforcement spring having an interior side facing the lumen and an exterior side facing away from the lumen. A malleable wire extends along the exterior side of the reinforcement spring, the malleable wire having a U-shape, the lower portion of the U-shape disposed at the distal end of the body.

Even further still, the invention relates to a malleable cannula having a body with a proximal end and a distal end, the body having a wall defining a lumen extending from the proximal end to the distal end. A reinforcement spring extends along the lumen and a malleable wire extends along the exterior side of the reinforcement spring, the reinforcement spring having a plurality of loops, each loop having an outwardly bowed portion shaped to accommodate the malleable wire between the reinforcement spring and the lumen without impacting the cross-sectional area of the lumen.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which:

FIG. 1 is a front elevation view of a cannula;

FIG. 2 is an enlarged perspective view of a segment of the distal end of a cannula according to a first embodiment of the invention, the segment location generally indicated by line 2-2 of FIG. 1;

FIG. 8 is an enlarged perspective view of a segment of the distal end of a cannula according to a fourth embodiment of the invention, the segment location generally indicated by line 2-2 of FIG. 1;

FIG. 9 is a sectional view taken generally along line 9-9 of FIG. 8;

FIG. 10 is an enlarged perspective view of a segment of the distal end of a cannula according to a fifth embodiment of the invention, the segment location generally indicated by line 2-2 of FIG. 1; and FIG. 11 is a sectional view of a cannula body according to a sixth embodiment of the invention.

DESCRIPTION OF PREFERRED EMBODIMENTS

Figure 3:
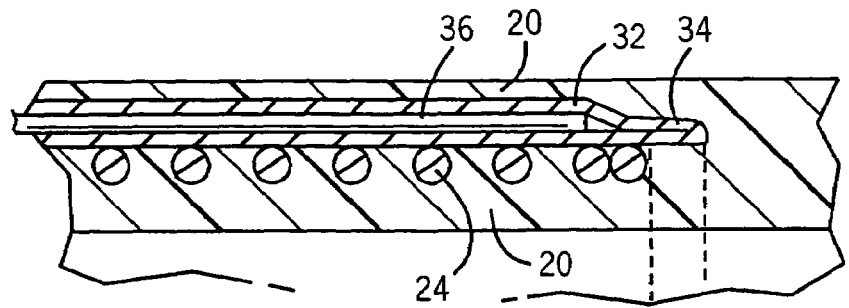
FIG. 3 is a sectional view taken generally along line 3-3 of FIG. 2.

Referring to FIG. 1, a catheter or cannula, shown as, but not limited to, venous cannula 10 has a proximal end 12 and a distal end 14. A tip 16 is located at the distal end 14 of the cannula 10 and a lumen 18 defined by a wall 20 extends through the cannula 10 from the proximal end 12 to the tip 16.

The lumen 18 may be open at the proximal end 12 to be connected to a cardiac bypass system such as a heart-lung machine. When cannula 10 is a venous cannula, the tip 16 includes a number of apertures 22 for draining blood from the heart to pass through the lumen 18 and into a heart-lung machine. Various methods of performing a cardiopulmonary bypass are known in the art. In the embodiment depicted in FIG. 1, the cannula is a single stage venous cannula having set of apertures 22 located at the distal end 14. In other embodiments, the cannula may be a dual stage venous cannula having two sets of apertures used to drain two portions of the heart simultaneously.

Referring to FIGS. 1 and 2, a reinforcement member, shown as helical reinforcement spring 24 may extend over a substantial portion of the length of cannula 10 to prevent kinking or closing off of the lumen 18 when the device is in use by a surgeon. In an exemplary embodiment, a malleable member 30 may extend along the length of reinforcement spring 24. Malleable member 30, like reinforcement spring 24, is embedded within wall 20.

A surgeon or other user may bend the cannula 10 into a desired shape by hand pressure. The malleable member 30 maintains the cannula in the bent shape chosen by the surgeon. The cannula may be bent again from the first desired shape into a second desired shape by hand pressure if that is deemed necessary, and the malleable member 30 will maintain the second desired shape. The bending of the cannula may be performed while fluid (e.g. blood) is flowing through the lumen 18 without interrupting the flow of fluid. Accordingly, the cannula may be shaped and reshaped during a surgical procedure while flood is flowing through the cannula without interruption of the surgical procedure. Bending or shaping of one portion of the cannula may be performed without altering the shape of other portions of the cannula.

When the cannula 10 is used as a venous cannula, the malleability discussed above is useful, especially where the surgeon desires a bend in the distal end 14 of the cannula (e.g. within 10 cm of the tip 16) to aid in the proper placement of the cannula within the heart. For example, the surgeon may desire to insert the cannula into an aperture in the right atrium of the heart and have a bend in the distal end 14 of the cannula to direct the tip 16 either up into the superior vena cava or down into the inferior vena cava. The cannula of the present invention may be used to replace a cannula having a permanent bend in the distal end. The use of a malleable cannula to permit a custom bend in the distal end of the cannula may be desirable when placing a patient on cardiopulmonary bypass prior to performing mitral or aortic valve replacement or repair.

Another reason for providing a malleable member 30 in the cannula 10 relates to improving the usage of space. A surgeon may wish to bend the cannula 10 to avoid interference with other surgical tools near the aperture into a patient's body. This is especially the case when performing minimally invasive surgical procedures having limited access space into the patient.

The malleable member 30 may extend over a substantial portion of the length of cannula 10, or may only extend along a particular portion for which malleability is desired. For example, in one embodiment, the malleable member 30 may extend over a portion (e.g. 5-15 cm) of the distal end of the cannula 10, to provide malleability to that portion, while the rest of the cannula remains resilient.

Referring to FIG. 2, in an exemplary embodiment, malleable member 30 includes a tube 32 that is formed into an anchor, shown as collar 34 at the distal end of the tube 32. In one embodiment, a wire 36 may be placed in tube 32 to provide additional support in maintaining cannula 10 in any particular shape chosen by the surgeon.

Collar 34 anchors malleable member 30 into place within wall 20 such that when cannula 10 is bent, twisted, and otherwise manipulated by a surgeon, malleable member 30 remains in place rather than sliding within wall 20, which can lead to undesired damage to wall 20. Collar 34 may be prevented from sliding toward proximal end 12 by the material in wall 20 as well as by direct interference with the distal end of the reinforcement spring 24.

Further referring to FIG. 2, the location of tube 32 on the exterior of reinforcement spring 24 results in a configuration that does not degrade the flow through lumen 18. Accordingly, for a cannula having a given outside diameter, the cross-sectional area of the lumen may be the same for both a cannula having a malleable member and one without.

Referring to FIG. 3, in a preferred embodiment, wire 36 extends through tube 32 up to the point at which tube 32 narrows to form collar 34. Collar 34 is a flattened portion of tube 32. Wire 36 and tube 32 are sized to permit easy insertion of wire 36 into tube 32 during the construction of cannula 10.

Figure 4:
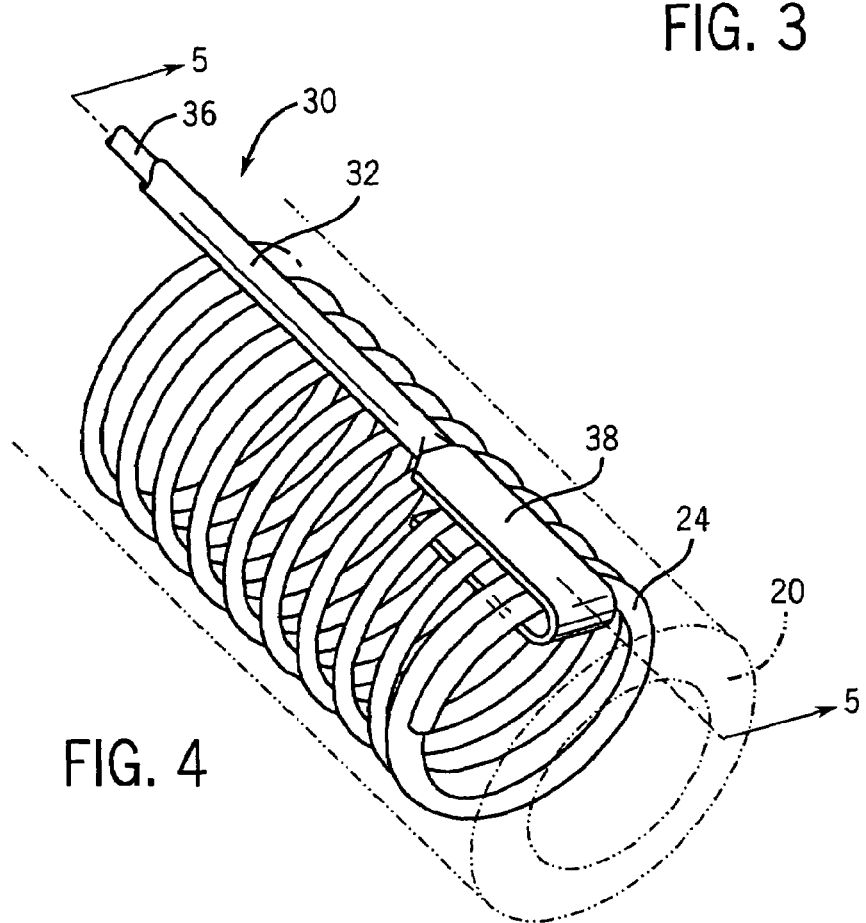
FIG. 4 is an enlarged perspective view of a segment of the distal end of a cannula according to a second embodiment of the invention, the segment location generally indicated by line 2-2 of FIG. 1.

Referring to FIG. 4, in another exemplary embodiment, the distal end of tube 32 may be flattened and formed into an anchor, shown as a hook 38 that wraps around the last few coils of the reinforcement spring 24. The hook 38, like the collar 34 shown in FIGS. 2 and 3, maintains malleable member 30 in place within wall 20 as the cannula 10 is manipulated by the surgeon.

Figure 5:
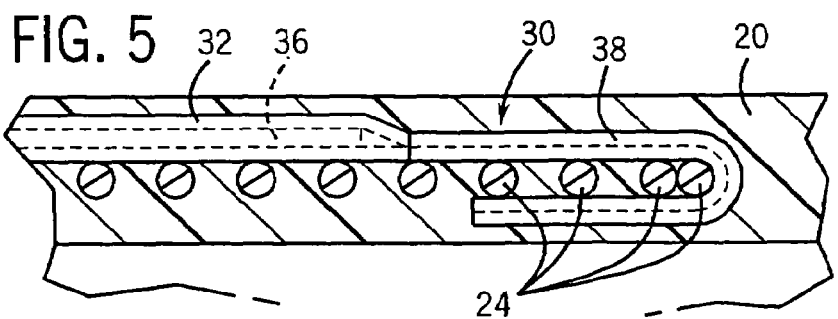
FIG. 5 is a sectional view taken generally along line 5-5 of FIG. 4.

Referring to FIG. 5, wire 36 extends through tube 32 to provide support to the malleable member 30. Wire 36 terminates at the location that tube 32 narrows to form hook 38. Hook 38 is shown as wrapping around the final four coils of reinforcement spring 24 but may wrap around fewer or more coils as desired or to provide additional anchoring of malleable member 30. The reinforcement spring 24 prevents malleable member 30 from shifting to the left in the reference frame of FIG. 5 and the material of wall 20 prevents malleable member 30 from shifting to the right, so the combination of reinforcement spring 24 and wall 20 anchors malleable member 30 into place.

Figure 6:
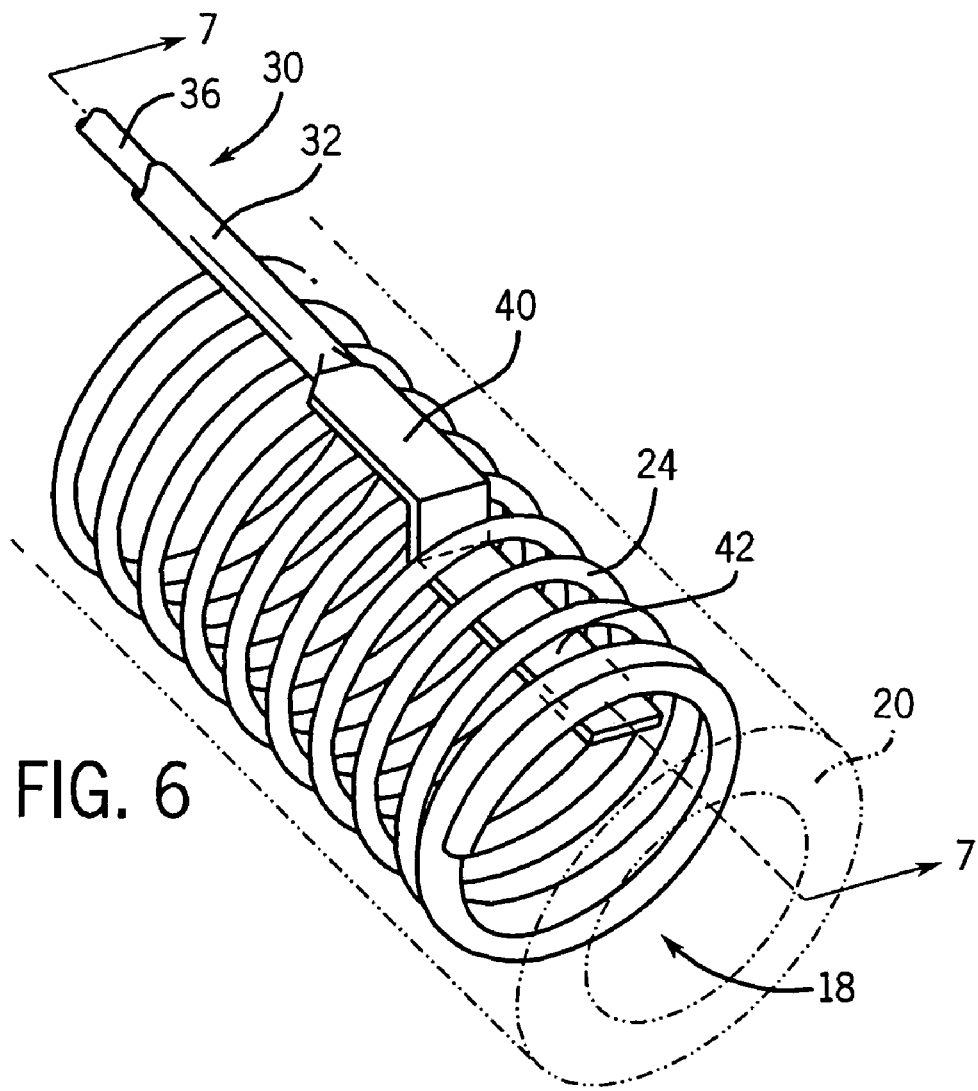
FIG. 6 is an enlarged perspective view of a segment of a distal end of a cannula according to a third embodiment of the invention, the segment location generally indicated by line 2-2 of FIG. 1.
Figure 7:
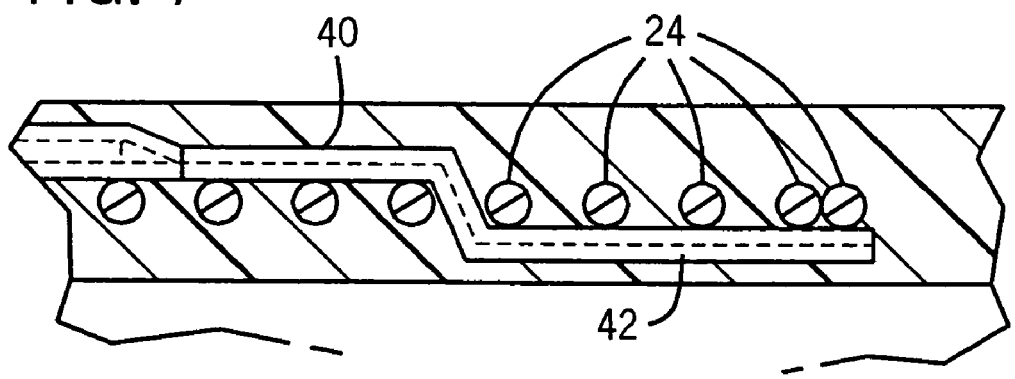
FIG. 7 is a sectional view taken generally along line 7-7 of FIG. 6.

Referring to FIGS. 6 and 7, in another exemplary embodiment of the invention, the distal end of malleable member 30 is flattened into an anchor, shown as a stepped portion having an upper step 40 and a lower step 42. The lower step may be tucked underneath the last few coils of reinforcement spring 24 in order to anchor malleable member 30 into place. The stepped portion therefore interlocks with the reinforcement spring 24 to anchor malleable member into place while the cannula is manipulated by the surgeon. As depicted in FIG. 7, in an exemplary embodiment, wire 36 extends through tube 32 up to the point at which the stepped portion begins. Preferably, the stepped portion is formed by flattening tube 32 without the wire 36 disposed therein.

Further referring to FIGS. 6 and 7, in contrast with the embodiments depicted in FIGS. 2-5, the lower step 42 is located on the lumen side of reinforcement spring 24. The number of coils that lower step 42 extends underneath is a design choice based upon the degree of desired anchoring and other considerations. The location of lower step on the interior side of reinforcement spring 24 has little effect on the cross-sectional area of lumen 18 due to the flattened design of the anchor.

Referring to FIGS. 8 and 9, in another exemplary embodiment of the invention, malleable member 30 may comprise a looped wire 44. The looped wire 44 is anchored into position with respect to wall 20 due to the fact that the material of wall 20 surrounds the distal end of looped wire 44, thus preventing substantial movement of looped wire 44 within wall 20.

Referring to FIG. 10, in another exemplary embodiment of the invention, malleable member 30 may include wire 36 slidably disposed within tube 32 and extending outwardly therefrom at the distal end of malleable member 30. Accordingly, a slip joint 46 is arranged at the point at which wire 36 enters tube 30 at the distal end. When a surgeon manipulates the cannula, the wire 36 may slide through slip joint 46 into tube 32 to relieve stress on the end 48 of wire 36 such that the end 48 is not forced through the material of wall 20, thus possibly damaging wall 20. In the embodiment of FIG. 10, the construction of malleable member 30 is such that stress is relieved through the relative sliding of wire 36 and tube 32 such that malleable member 30 need not be solidly anchored with respect to wall 20 as in the embodiments depicted in FIGS. 2-8.

Referring to FIG. 11, in another exemplary embodiment of the invention, the reinforcement spring 24 may be shaped to create extra room such that malleable member 30 may be disposed on the interior side of reinforcement spring 24 without negatively impacting the cross-sectional area of lumen 18. In the embodiment of FIG. 11, malleable member 30 may be made of a single solid wire.

A cannula, such as that depicted in FIG. 1, may be made by providing a stainless steel mandrel and dipping it into a plastic material, such as liquid plastisol. The initial layer of plastisol may then be cured (at least partially) in an oven. The reinforcement spring 24 (with or without the malleable member coupled thereto) may then be slipped over the first layer of plastisol (with the mandrel still in place underneath the initial layer of plastisol). If added separately, the malleable member may then placed on the exterior of the reinforcement spring through the use of a small amount of liquid plastisol to "weld" the malleable member into place.

In the embodiments of FIGS. 4 and 6, the anchor (i.e. the hook or stepped portion) may aid in maintaining the placement of the malleable member over the reinforcement spring before the next layer of plastisol is applied. Once the reinforcement spring and malleable member are in place, the mandrel is again dipped into liquid plastisol to add another layer of wall material, a step that is performed as many additional times as necessary to create the desired wall thickness. It may be desirable to only partially cure the individual layers before adding additional layers to provide for additional adhesion between adjacent layers. Once the cannula construction is complete, the layers may be fully cured. Pressurized alcohol is then typically injected to release the finished cannula from the mandrel.

Other methods of cannula construction are known in the art. For example, another method of making a cannula according to an embodiment of the present invention is to utilize a series of layers of extruded tubing. The reinforcement spring and malleable member may be added between adjacent layers of the tubing, which are slidably added during construction of the cannula.

The materials used to construct the different cannula embodiments disclosed herein are generally known in the art. For example, the plastisol used to form the wall in the dip molding process described above is a liquid vinyl dispersion that is fused by heat to form a solid end product. Other plastic materials may also be suitable. The reinforcement spring is typically made of stainless steel as are the parts of the malleable member. In a preferred embodiment, the tube of the malleable member is made of 304 stainless steel while the wire inserted within the tube (in those embodiments having such a structure) is made of 302 stainless steel.

The collar, hook, and stepped anchors at the distal end of the malleable member depicted in FIGS. 2, 4, and 6 are made, in an exemplary embodiment, by flattening and shaping the end portion of the hollow tube 32. This method of construction alleviates work hardening concerns and other materials difficulties that occur when shaping a solid stainless steel wire into the anchor forms. A large amount of compressive force is required to shape a solid wire into an anchor, while a tube may be flattened and shaped much more easily, without resulting in the brittleness that results from work hardening. Further, flattening the tube to create the various anchors eliminates the pointed end of the wire or tube that may otherwise present an increased risk of damage to the cannula wall.

When using the wire and tube construction of the malleable member, the distal end of the tube is first flattened and formed into the desired shape. The wire is then inserted into the tube to provide the desired rigidity and mass to malleable member 30. The tube 32 is sized to slidably receive wire 36 during the construction process.

While the detailed drawings and specific examples given describe various exemplary embodiments, they serve the purpose of illustration only. It is to be understood that the invention is not limited in its application to the details of construction and arrangements of components set forth in the preceding description or illustrated in the drawings. For example, while a venous cannula is shown incorporating the various aspects of the invention, the invention may also be applicable to arterial cannulae, cardioplegia cannulae, or other cannula and catheter designs that are intended to be malleable. Such cannulae are available in many sizes and shapes and used in different types of surgical procedures. Furthermore, other substitutions, modifications, changes, and omissions may be made in the design, operating conditions, and arrangements of the exemplary embodiments without departing from the scope of the invention as expressed in the appended claims.

What is claimed is:

1. A method of making a malleable cannula, comprising the steps of:
   providing a mandrel and a quantity of a molten plastic material;
   dipping the mandrel into the plastic material to coat the mandrel with a first layer of the plastic material;
   sliding a reinforcement spring over the first layer;
   providing a malleable member comprising a tubular structure;
   flattening the tubular structure at a distal end thereof in order to form a non-planar anchor;
   coupling the malleable member to the exterior side of the reinforcement spring; and
   dipping the mandrel into the plastic material to coat the mandrel with a second layer of the plastic material.

2. The method of claim 1, wherein the malleable member further comprises a wire slidably disposed within the tubular structure.

3. The method of claim 2, wherein the anchor is a collar constructed of a flattened portion of the tubular structure and wherein the wire does not extend into the collar.

4. The method of claim 2, wherein the anchor is a hook constructed of a flattened portion of the tubular structure and wherein the wire does not extend into the hook.

5. The method of claim 2, wherein the anchor is a stepped portion constructed of a flattened portion of the tubular structure and wherein the wire does not extend into the stepped portion.

6. The method of claim 1, further comprising the step of injecting pressurized alcohol into the mandrel to release the malleable cannula.

7. The method of claim 1, wherein the plastic material is plastisol.

8. The method of claim 1, wherein the malleable member is added to the reinforcement spring by using the liquid plastic material as an adhesive.

* * * * *